(12) United States Patent
Koike

(10) Patent No.: US 12,419,590 B2
(45) Date of Patent: Sep. 23, 2025

(54) IMAGE PROCESSING DEVICE, IMAGE PROCESSING METHOD, AND IMAGE PROCESSING PROGRAM

(71) Applicant: FUJIFILM Corporation, Tokyo (JP)

(72) Inventor: Takafumi Koike, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 350 days.

(21) Appl. No.: 18/183,858

(22) Filed: Mar. 14, 2023

(65) Prior Publication Data

US 2023/0215057 A1 Jul. 6, 2023

Related U.S. Application Data

(63) Continuation of application No. PCT/JP2021/027309, filed on Jul. 21, 2021.

(30) Foreign Application Priority Data

Sep. 30, 2020 (JP) .................................. 2020-166473

(51) Int. Cl.
*A61B 6/02* (2006.01)
*G06T 7/00* (2017.01)
(Continued)

(52) U.S. Cl.
CPC ............ *A61B 6/025* (2013.01); *G06T 7/0012* (2013.01); *G06T 7/11* (2017.01); *G06T 11/003* (2013.01); *G06T 2207/30068* (2013.01)

(58) Field of Classification Search
None
See application file for complete search history.

(56) References Cited

U.S. PATENT DOCUMENTS

2009/0123052 A1 5/2009 Ruth et al.
2011/0109650 A1 5/2011 Kreeger et al.
(Continued)

FOREIGN PATENT DOCUMENTS

JP 2014-128716 A 7/2014
JP 2020-512129 A 4/2020
JP 2020-096752 A 6/2020

OTHER PUBLICATIONS

The extended European search report issued by the European Patent Office on Feb. 28, 2024, which corresponds to European Patent Application No. 21874874.7-1126 and is related to U.S. Appl. No. 18/183,858.

(Continued)

*Primary Examiner* — Helen Zong
(74) *Attorney, Agent, or Firm* — Studebaker Brackett PLLC

(57) ABSTRACT

An image processing device determines whether each tumor candidate regions detected from a plurality of tomographic images indicating a plurality of tomographic planes of an object is a tumor or a local mass of a mammary gland, selects a first tomographic image group from the plurality of tomographic images in a first region determined to be the tumor, selects a second tomographic image group from the plurality of tomographic images in a second region determined to be the local mass of the mammary gland, selects a third tomographic image group from the plurality of tomographic images in a third region other than the first region and the second region, and generates a composite two-dimensional image using the tomographic image groups selected for each of the first region, the second region, and the third region.

14 Claims, 7 Drawing Sheets

(51) Int. Cl.
*G06T 7/11* (2017.01)
*G06T 11/00* (2006.01)

(56) References Cited

U.S. PATENT DOCUMENTS

| | | |
|---|---|---|
| 2014/0033126 A1 | 1/2014 | Kreeger et al. |
| 2016/0206268 A1 | 7/2016 | Fukuda |
| 2017/0011534 A1 | 1/2017 | Costa et al. |
| 2019/0083051 A1* | 3/2019 | Shimada .............. A61B 6/5235 |
| 2020/0043172 A1* | 2/2020 | Ito ......................... G06T 7/0014 |
| 2021/0118199 A1 | 4/2021 | Chui et al. |
| 2023/0214977 A1* | 7/2023 | Okumura ............. A61B 6/5217 |
| | | 382/131 |

OTHER PUBLICATIONS

International Search Report issued in PCT/JP2021/027309; mailed Sep. 21, 2021.
International Preliminary Report on Patentability (Chapter I) and Written Opinion of the International Searching Authority issued in PCT/JP2021/027309; issued Mar. 28, 2023.

* cited by examiner

IMAGE PROCESSING DEVICE, IMAGE PROCESSING METHOD, AND IMAGE PROCESSING PROGRAM

CROSS-REFERENCE TO RELATED APPLICATIONS

This application is a continuation application of International Application No. PCT/JP2021/027309 filed Jul. 21, 2021 the disclosure of which is incorporated herein by reference in its entirety. Further, this application claims priorities from Japanese Patent Application No. 2020-166473, filed Sep. 30, 2020, the disclosure of which is incorporated herein by reference in their entirety.

TECHNICAL FIELD

The present disclosure relates to an image processing device, an image processing method, and an image processing program.

RELATED ART

In recent years, image diagnosis using a radiography apparatus (called mammography) for capturing an image of a breast has attracted attention in order to promote early detection of breast cancer. Further, in the mammography, tomosynthesis imaging has been proposed which moves a radiation source, irradiates the breast with radiation at a plurality of radiation source positions to acquire a plurality of projection images, and reconstructs the acquired plurality of projection images to generate tomographic images in which desired tomographic planes have been highlighted. In the tomosynthesis imaging, the radiation source is moved in parallel to a radiation detector or is moved to draw a circular or elliptical arc, according to the characteristics of an imaging apparatus and the required tomographic images, and the breast is imaged at a plurality of radiation source positions to acquire a plurality of projection images. Then, the acquired plurality of projection images are reconstructed, using a back projection method, such as a simple back projection method or a filtered back projection method, or an iterative reconstruction method, to generate tomographic images.

The tomographic images are generated in a plurality of tomographic planes of the breast, which makes it possible to separate structures that overlap each other in a depth direction in which the tomographic planes are arranged in the breast. Therefore, it is possible to find an abnormal part, such as a lesion, that has been difficult to detect in a two-dimensional image (hereinafter, referred to as a simple two-dimensional image) acquired by simple imaging according to the related art which irradiates an object with radiation in a predetermined direction.

In addition, a technique is known which combines a plurality of tomographic images having different distances (positions in a height direction) from a detection surface of a radiation detector to a radiation source, which have been acquired by tomosynthesis imaging, using, for example, an addition method, an averaging method, a maximum intensity projection method, or a minimum intensity projection method, to generate a pseudo two-dimensional image (hereinafter, referred to as a "composite two-dimensional image") corresponding to the simple two-dimensional image (see JP2014-128716A).

In addition, a technique is known which detects a tumor lesion and a normal breast structure from a tomographic image, represents the tumor lesion on a composite two-dimensional image such that the tumor lesion is more highlighted than the normal breast structure, and represents the normal breast structure on the composite two-dimensional image such that it indicates a simple two-dimensional image (see JP2020-512129A).

However, for example, the local mass of the mammary gland that looks like the tumor lesion in the simple two-dimensional image still looks like the tumor lesion in the composite two-dimensional image according to the related art generated by the method described in JP2020-512129A. That is, in some cases, in the composite two-dimensional image according to the related art, the same diagnostic performance as the tomographic image is not obtained. Therefore, a diagnostician, such as a doctor, interprets not only the composite two-dimensional image but also a large number of tomographic images, which increases an interpretation burden.

SUMMARY

The present disclosure has been made in view of the above circumstances, and an object of the present disclosure is to provide an image processing device, an image processing method, and an image processing program that can generate a composite two-dimensional image having the same diagnostic performance as a tomographic image.

According to the present disclosure, there is provided an image processing device comprising at least one processor. The processor detects a tumor candidate region from a plurality of tomographic images indicating a plurality of tomographic planes of an object, determines whether each of the detected tumor candidate regions is a tumor or a local mass of a mammary gland, selects a first tomographic image group from the plurality of tomographic images in a first region determined to be the tumor, selects a second tomographic image group from the plurality of tomographic images in a second region determined to be the local mass of the mammary gland, selects a third tomographic image group from the plurality of tomographic images in a third region other than the first region and the second region, and generates a composite two-dimensional image using the tomographic image groups selected for each of the first region, the second region, and the third region.

In addition, in the image processing device according to the present disclosure, the first tomographic image group may be a tomographic image group in which the tumor candidate region determined to be the tumor is detected among the plurality of tomographic images.

Further, in the image processing device according to the present disclosure, the second tomographic image group may be a tomographic image group other than a tomographic image in which the tumor candidate region determined to be the local mass of the mammary gland is detected among the plurality of tomographic images.

Furthermore, in the image processing device according to the present disclosure, the second tomographic image group may include a tomographic image in which the tumor candidate region determined to be the local mass of the mammary gland is detected and a tomographic image of a layer adjacent to the tomographic image among the plurality of tomographic images.

Moreover, in the image processing device according to the present disclosure, the second tomographic image group may be the same tomographic image group as the third tomographic image group, and the processor may generate the composite two-dimensional image in which a density of the second region has been controlled to be close to a density of the third region.

In addition, in the image processing device according to the present disclosure, the third tomographic image group may be all of the plurality of tomographic images, a tomographic image group, in which an absolute value of a difference between a pixel value of a pixel of interest and an average value of the pixel values of the pixels of interest in all of the plurality of tomographic images is equal to or greater than a preset threshold value, among the plurality of tomographic images, a group of a preset number of tomographic images in a descending order of a variance value of a pixel value of a region of interest including the pixel of interest among the plurality of tomographic images, or a tomographic image group including a pixel whose edge is detected by an edge detection process among the plurality of tomographic images.

Further, in the image processing device according to the present disclosure, the processor may perform control to display the generated composite two-dimensional image and perform control to display a determination result of whether the tumor candidate region is the tumor or the local mass of the mammary gland on the composite two-dimensional image.

Furthermore, according to the present disclosure, there is provided an image processing method executed by a processor included in an image processing device. The image processing method comprises: detecting a tumor candidate region from a plurality of tomographic images indicating a plurality of tomographic planes of an object; determining whether each of the detected tumor candidate regions is a tumor or a local mass of a mammary gland; selecting a first tomographic image group from the plurality of tomographic images in a first region determined to be the tumor; selecting a second tomographic image group from the plurality of tomographic images in a second region determined to be the local mass of the mammary gland; selecting a third tomographic image group from the plurality of tomographic images in a third region other than the first region and the second region; and generating a composite two-dimensional image using the tomographic image groups selected for each of the first region, the second region, and the third region.

Moreover, according to the present disclosure, there is provided an image processing program that causes a processor included in an image processing device to execute a process comprising: detecting a tumor candidate region from a plurality of tomographic images indicating a plurality of tomographic planes of an object; determining whether each of the detected tumor candidate regions is a tumor or a local mass of a mammary gland; selecting a first tomographic image group from the plurality of tomographic images in a first region determined to be the tumor; selecting a second tomographic image group from the plurality of tomographic images in a second region determined to be the local mass of the mammary gland; selecting a third tomographic image group from the plurality of tomographic images in a third region other than the first region and the second region; and generating a composite two-dimensional image using the tomographic image groups selected for each of the first region, the second region, and the third region.

According to the present disclosure, it is possible to generate a composite two-dimensional image having the same diagnostic performance as a tomographic image.

DETAILED DESCRIPTION

Hereinafter, an embodiment for carrying out the technology of the present disclosure will be described in detail with reference to the drawings.

Figure 1:
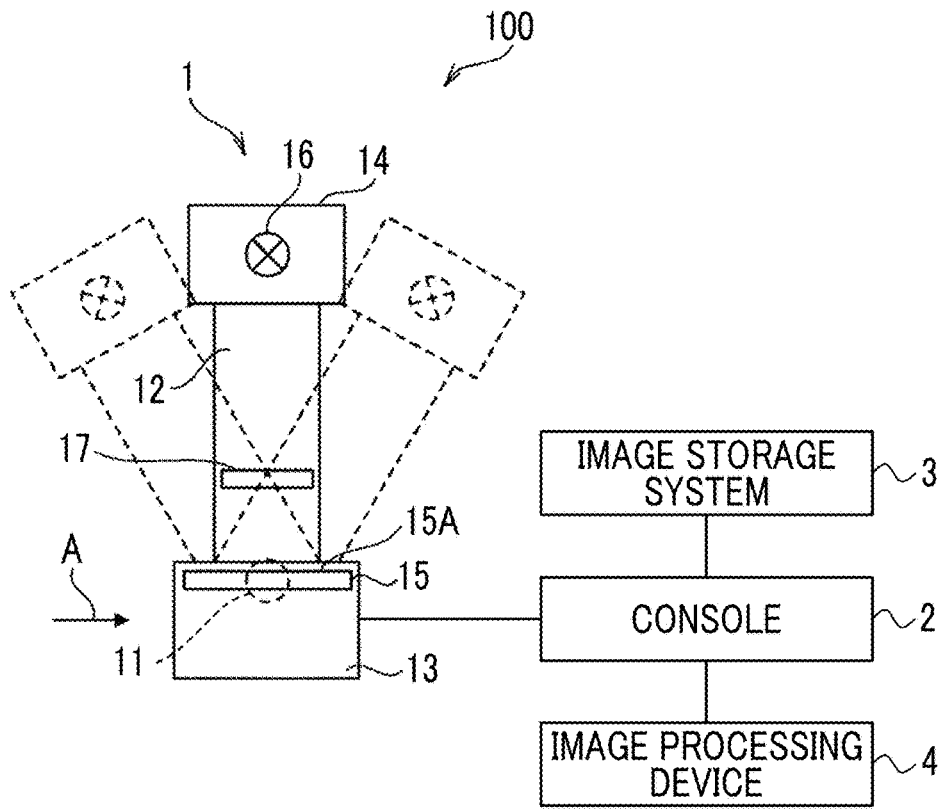
FIG. 1 is a diagram schematically illustrating a configuration of a radiography system.
Figure 2:
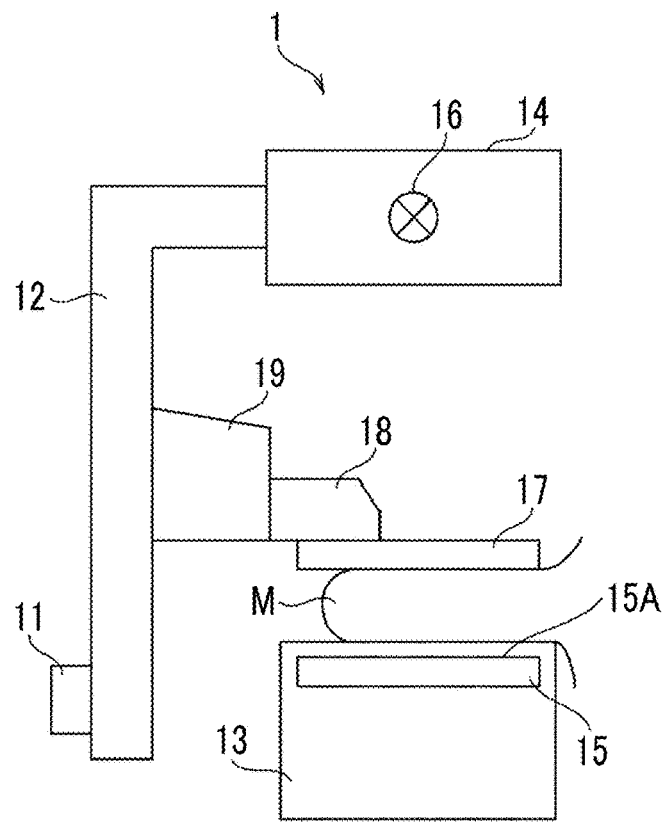
FIG. 2 is a diagram illustrating a radiography apparatus as viewed from a direction of an arrow A in FIG. 1.

First, a configuration of a radiography system 100 according to this embodiment will be described with reference to FIGS. 1 and 2. As illustrated in FIGS. 1 and 2, the radiography system 100 images a breast M, which is an object, at a plurality of radiation source positions and acquires a plurality of radiographic images, that is, a plurality of projection images, in order to perform tomosynthesis imaging on the breast to generate tomographic images. The radiography system 100 comprises a mammography apparatus 1, a console 2, an image storage system 3, and an image processing device 4.

The mammography apparatus 1 comprises an arm portion 12 that is connected to a base (not illustrated) by a rotation shaft 11. An imaging table 13 is attached to one end of the arm portion 12, and a radiation emitting unit 14 is attached to the other end of the arm portion 12 to face the imaging table 13. The arm portion 12 is configured such that only the end to which the radiation emitting unit 14 is attached can be rotated. Therefore, the imaging table 13 is fixed, and only the radiation emitting unit 14 can be rotated.

A radiation detector 15, such as a flat panel detector, is provided in the imaging table 13. The radiation detector 15 has a radiation detection surface 15A. In addition, for example, a circuit substrate including a charge amplifier that converts a charge signal read from the radiation detector 15 into a voltage signal, a correlated double sampling circuit that samples the voltage signal output from the charge amplifier, and an analog-to-digital (AD) conversion unit that converts the voltage signal into a digital signal is provided in the imaging table 13.

A radiation source 16 is accommodated in the radiation emitting unit 14. The radiation source 16 emits, for example, X-rays as radiation. The console 2 controls the time when the radiation source 16 emits the radiation and the radiation generation conditions of the radiation source 16, that is, the selection of materials of a target and a filter, a tube voltage, an irradiation time, and the like.

Further, the arm portion 12 is provided with a compression plate 17 that is disposed above the imaging table 13 and presses and compresses the breast M, a support portion 18 that supports the compression plate 17, and a movement mechanism 19 that moves the support portion 18 in an up-down direction in FIGS. 1 and 2. Furthermore, an interval between the compression plate 17 and the imaging table 13, that is, the thickness of the compressed breast is input to the console 2.

The console 2 has a function of controlling the mammography apparatus 1 using, for example, an imaging order and various kinds of information acquired from a radiology information system (RIS) (not illustrated) or the like through a network, such as a wireless communication local area network (LAN), and instructions or the like directly issued by an engineer or the like. Specifically, the console 2 directs the mammography apparatus 1 to perform the tomosynthesis imaging on the breast M, acquires a plurality of projection images as described below, and reconstructs the plurality of projection images to generate a plurality of tomographic images. For example, in this embodiment, a server computer is used as the console 2.

The image storage system 3 is a system that stores image data such as radiographic images and tomographic images captured by the mammography apparatus 1. The image storage system 3 extracts image data corresponding to a request from, for example, the console 2 and the image processing device 4 from the stored image data and transmits the image data to a device that is the source of the request. A specific example of the image storage system 3 is a picture archiving and communication system (PACS).

Figure 3:
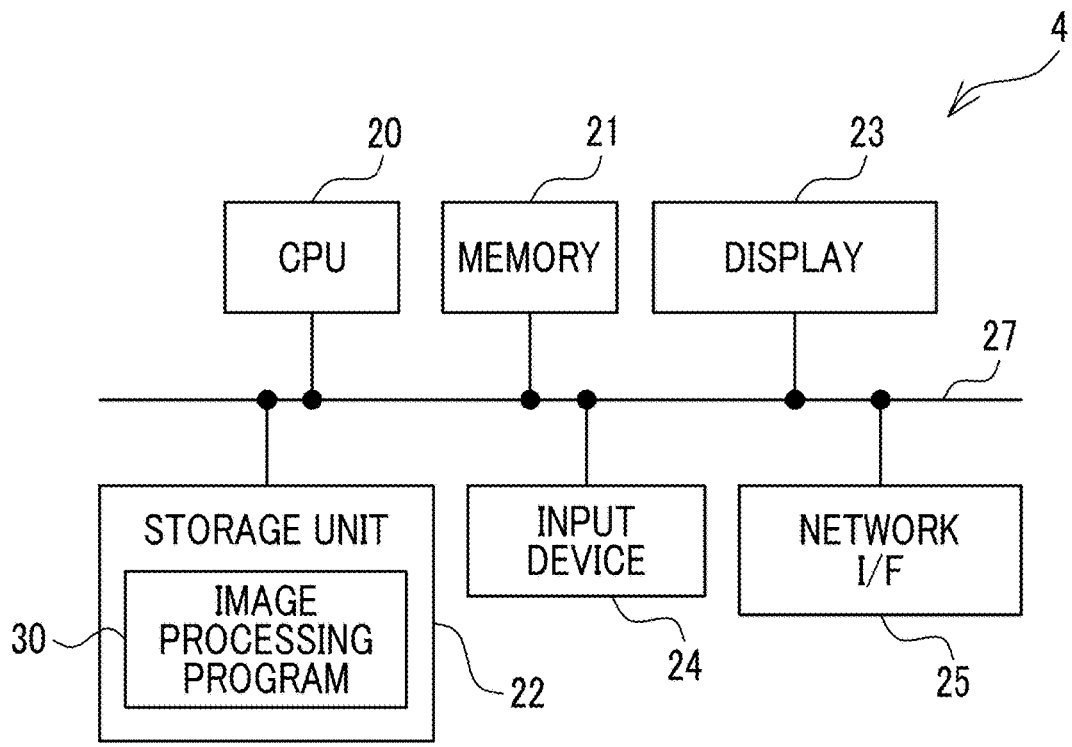
FIG. 3 is a block diagram illustrating an example of a hardware configuration of an image processing device.

Next, a hardware configuration of the image processing device 4 according to this embodiment will be described with reference to FIG. 3. As illustrated in FIG. 3, the image processing device 4 includes a central processing unit (CPU) 20, a memory 21 as a temporary storage area, and a non-volatile storage unit 22. In addition, the image processing device 4 includes a display 23, such as a liquid crystal display, an input device 24, such as a keyboard and a mouse, and a network interface (I/F) 25 that is connected to the network. The CPU 20, the memory 21, the storage unit 22, the display 23, the input device 24, and the network I/F 25 are connected to a bus 27.

The storage unit 22 is implemented by, for example, a hard disk drive (HDD), a solid state drive (SSD), or a flash memory. An image processing program 30 is stored in the storage unit 22 as a storage medium. The CPU 20 reads out the image processing program 30 from the storage unit 22, expands the image processing program 30 in the memory 21, and executes the expanded image processing program 30.

Figure 4:
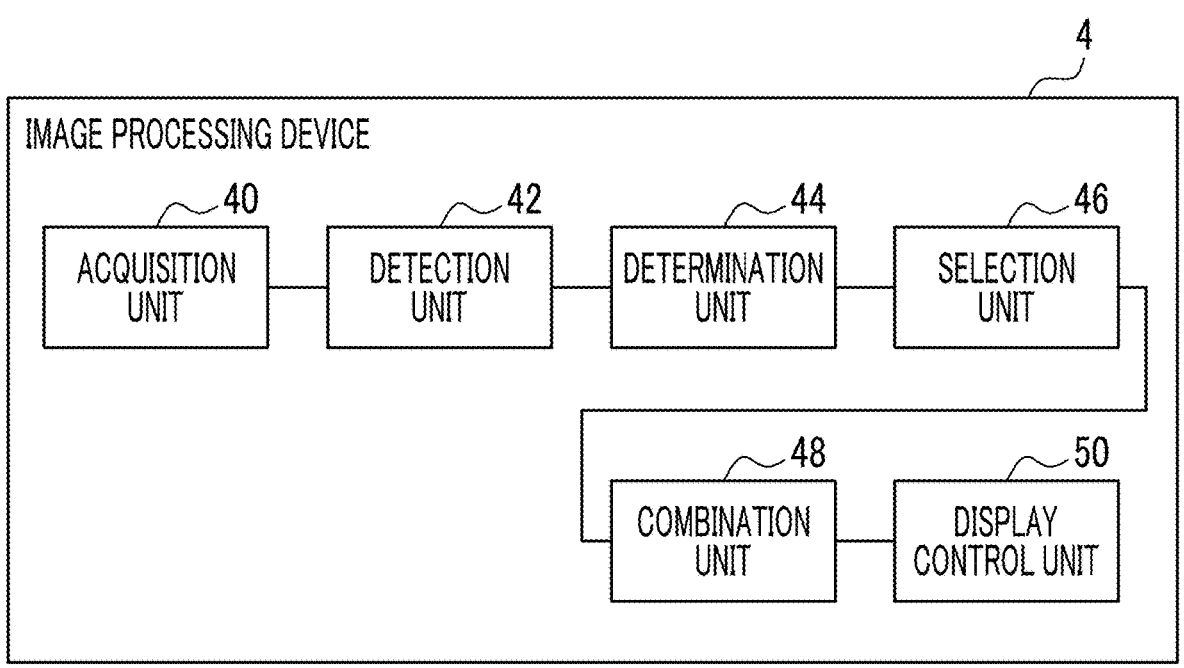
FIG. 4 is a block diagram illustrating an example of a functional configuration of the image processing device.

Next, the functional configuration of the image processing device 4 according to this embodiment will be described with reference to FIG. 4. As illustrated in FIG. 4, the image processing device 4 includes an acquisition unit 40, a detection unit 42, a determination unit 44, a selection unit 46, a combination unit 48, and a display control unit 50. The CPU 20 executes the image processing program 30 to function as the acquisition unit 40, the detection unit 42, the determination unit 44, the selection unit 46, the combination unit 48, and the display control unit 50.

The acquisition unit 40 acquires a plurality of tomographic images generated by the tomosynthesis imaging performed by the mammography apparatus 1 under the control of the console 2. The acquisition unit 40 acquires a plurality of tomographic images from the console 2 or the image storage system 3 through the network I/F 25.

Here, the tomosynthesis imaging and a tomographic image generation process in the console 2 will be described. The console 2 rotates the arm portion 12 on the rotation shaft 11 to move the radiation source 16 in a case in which the tomosynthesis imaging for generating tomographic images is performed. Further, the console 2 performs control to irradiate the breast M, which is the object, with the radiation under predetermined imaging conditions for tomosynthesis imaging at a plurality of radiation source positions by the movement of the radiation source 16. Further, the console 2 acquires a plurality of projection images Gi (i=1 to n; n is the number of radiation source positions, for example, n=15) at the plurality of radiation source positions which have been obtained by the detection of the radiation transmitted through the breast M by the radiation detector 15.

Figure 5:
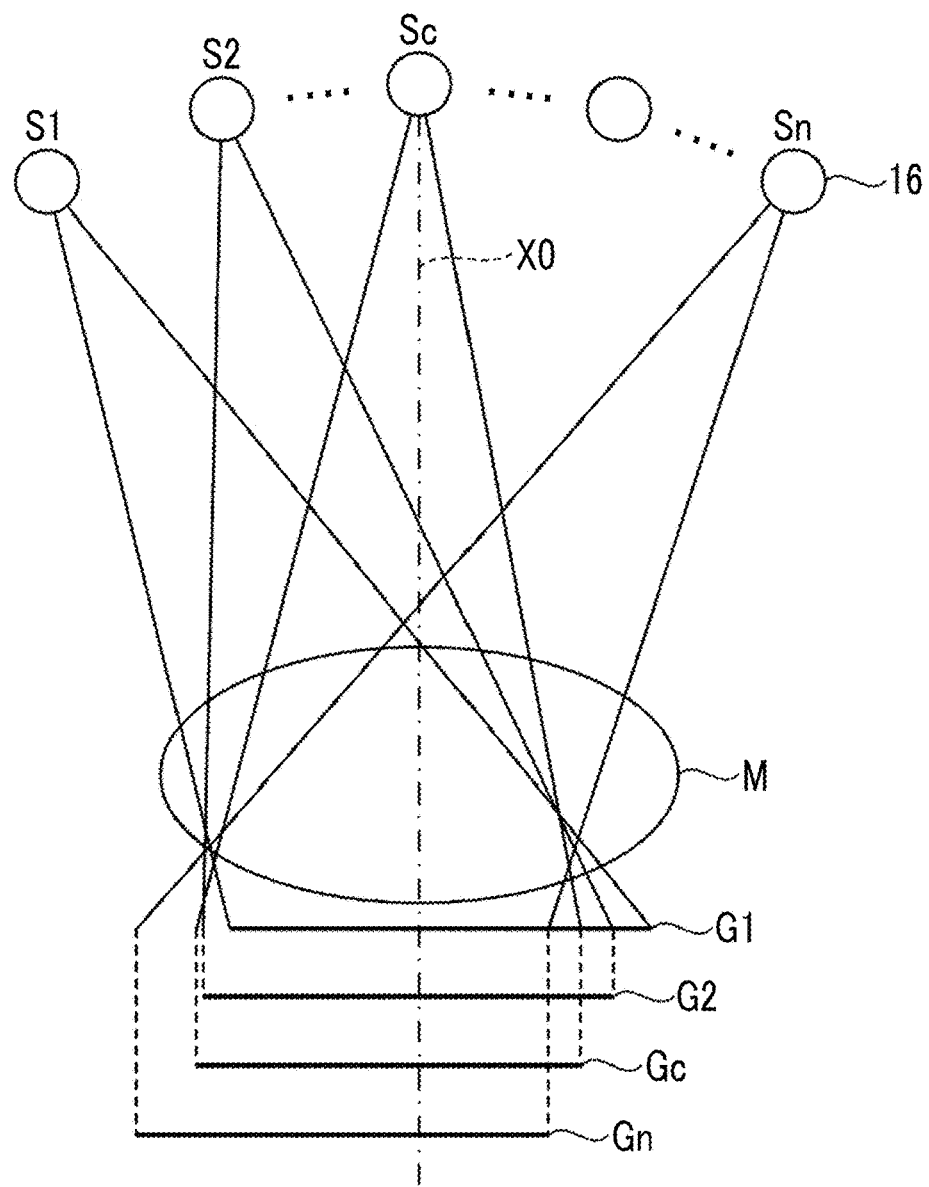
FIG. 5 is a diagram illustrating a projection image acquisition process.

As illustrated in FIG. 5, the radiation source 16 is moved to each of radiation source positions Si (i=1 to n). Then, the radiation source 16 is driven at each of the radiation source positions to irradiate the breast M with radiation. The radiation detector 15 detects the radiation transmitted through the breast M to acquire the projection images G1, G2, . . . , Gn corresponding to the radiation source positions S1 to Sn, respectively. In addition, at each of the radiation source positions S1 to Sn, the breast M is irradiated with the same dose of radiation.

Further, in FIG. 5, a radiation source position Sc is a radiation source position where an optical axis X0 of the radiation emitted from the radiation source 16 is orthogonal to the detection surface 15A of the radiation detector 15. Hereinafter, the radiation source position Sc is referred to as a reference radiation source position Sc.

Figure 6:
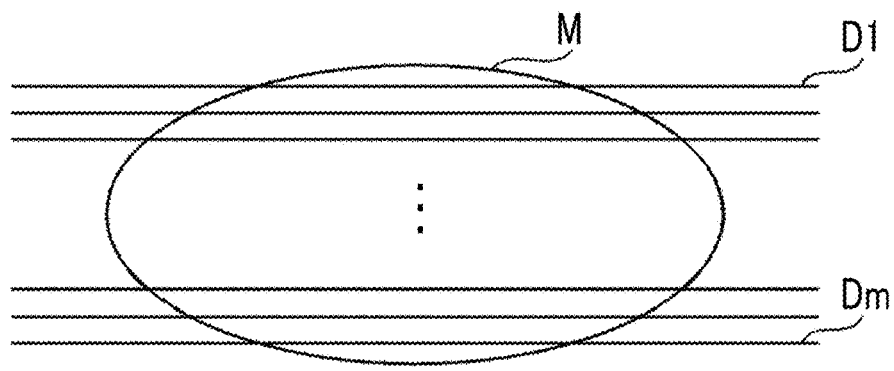
FIG. 6 is a diagram illustrating a tomographic image generation process.

The console 2 reconstructs the plurality of projection images Gi to generate a plurality of tomographic images in which the desired tomographic planes of the breast M have been highlighted. Specifically, the console 2 reconstructs the plurality of projection images Gi using a well-known back projection method such as a simple back projection method or a filtered back projection method. Therefore, as illustrated in FIG. 6, the console 2 generates a plurality of tomographic images Dj (j=1 to m) indicating each of a plurality of tomographic planes of the breast M. In this case, a three-dimensional coordinate position in a three-dimensional space including the breast M is set, and the pixel values of the corresponding pixels in the plurality of projection images Gi are reconstructed for the set three-dimensional coordinate position to calculate a pixel value at the coordinate position.

The console 2 transmits the generated tomographic images Dj to the image processing device 4 or the image storage system 3.

Figure 7:
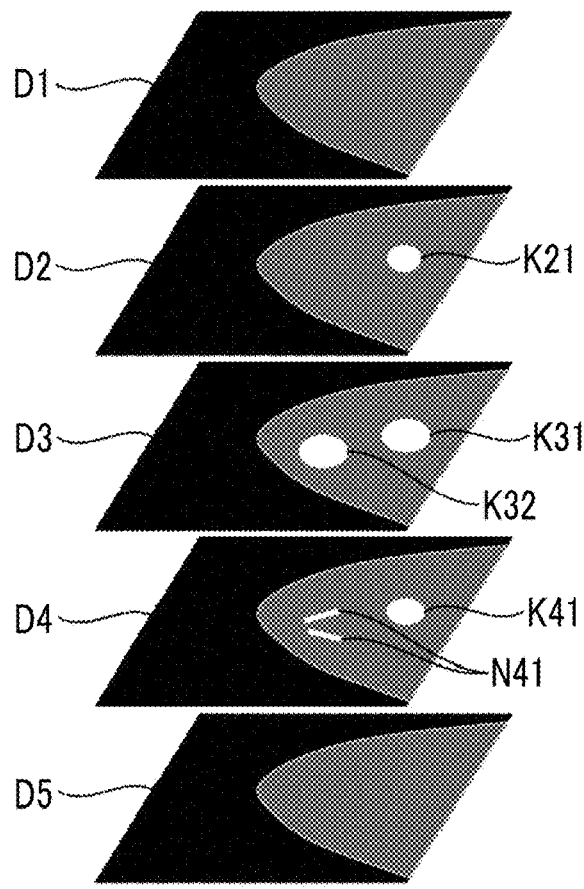
FIG. 7 is a diagram illustrating an example of a plurality of tomographic images.

As illustrated in FIG. 7, the detection unit 42 detects a tumor candidate region from the plurality of tomographic images Dj acquired by the acquisition unit 40. FIG. 7 illustrates a case in which the number of tomographic images Dj is 5 (that is, j=1 to 5) for simplicity of description. Further, in an example illustrated in FIG. 7, the tomographic image D2 includes a tumor candidate region K21, the tomographic image D3 includes tumor candidate regions K31 and K32, and the tomographic image D4 includes a tumor candidate region K41. In addition, in the example illustrated in FIG. 7, the tomographic image D4 includes a mammary gland N41. Further, it is assumed that the positions of the centers of gravity of the tumor candidate region K21, the tumor candidate region K31, and the tumor candidate region K41 are substantially the same in the tomographic images Dj. Furthermore, in the example illustrated in FIG. 7, the tumor candidate region K21, the tumor candidate region K31, and the tumor candidate region K41 are tumors, and the tumor candidate region K32 is a local mass of the mammary gland.

The detection unit 42 detects the tumor candidate region from each of the plurality of tomographic images Dj using a known algorithm for detecting a tumor using computer aided diagnosis (CAD). In the algorithm for detecting a tumor using CAD, a probability (likelihood) indicating that a pixel in the tomographic images Dj is the tumor candidate region is derived, and a pixel with a probability equal to or greater than a predetermined threshold value is detected as the tumor candidate region. Since it is difficult to distinguish between the tumor and the local mass of the mammary gland with only one tomographic image Dj, the local mass of the mammary gland is also detected as the tumor candidate region.

In addition, the detection of the tumor candidate region is not limited to the detection using CAD. The tumor candidate region may be detected from the tomographic images Dj by, for example, a filtering process using a filter for detecting the tumor candidate region or a detection model which has been subjected to machine learning using deep learning or the like to detect the tumor candidate region.

The determination unit 44 determines whether each of the tumor candidate regions detected by the detection unit 42 is the tumor or the local mass of the mammary gland. Since the tumor has a three-dimensional structure which occurs due to the proliferation of cancer cells and is filled with the cancer cells, the tumor appears over a plurality of consecutive tomographic images Dj among the tomographic images Dj. Meanwhile, since the local mass of the mammary gland has a structure in which thin extending mammary glands overlap each other, the local mass of the mammary gland appears as the tumor in one tomographic image Dj and appears as a normal mammary gland in the tomographic images Dj of adjacent layers.

Therefore, the determination unit 44 according to this embodiment determines the tumor candidate region, which appears in a plurality of consecutive tomographic images Dj and whose center of gravity is located substantially at the same position in each of the tomographic images Dj, to be the tumor. Here, substantially the same position of the center of gravity means that, for example, the distance between the positions of the centers of gravity of the tumor appearing in each of the plurality of tomographic images Dj is equal to or less than a predetermined threshold value. As the threshold value in this case, for example, a preset value can be applied as an upper limit value of the distance between the positions of the centers of gravity of the tumor appearing in a plurality of consecutive tomographic images Dj. In addition, the determination unit 44 determines the tumor candidate region, which does not appear in the tomographic images Dj of adjacent layers and appears in only one tomographic image Dj, to be the local mass of the mammary gland.

In the example illustrated in FIG. 7, the determination unit 44 determines the tumor candidate regions K21, K31, and K41 to be the tumor since the tumor candidate regions K21, K31, and K41 appear in the consecutive tomographic images D2 to D4 and the positions of the centers of gravity thereof are substantially the same in the tomographic images D2 to D4. In addition, in the example illustrated in FIG. 7, the determination unit 44 determines the tumor candidate region K32 appearing in the tomographic image D3 to be the local mass of the mammary gland since the tumor candidate region K32 does not appear substantially at the same position in the tomographic images D2 and D4 of the layers adjacent to the tomographic image D3.

The selection unit 46 selects a first tomographic image group from the plurality of tomographic images Dj in a first region determined to be the tumor by the determination unit 44. In this selection, the selection unit 46 selects the first tomographic image group according to a first selection rule. The first selection rule according to this embodiment is a rule of selecting a tomographic image group, in which the tumor candidate region determined to be the tumor by the determination unit 44 is detected, among the plurality of tomographic images Dj. In the example illustrated in FIG. 7, the selection unit 46 selects the tomographic images D2 to D4, in which the tumor candidate regions K21, K31, and K41 are detected, as the first tomographic image group.

The selection unit 46 selects a second tomographic image group from the plurality of tomographic images Dj in a second region determined to be the local mass of the mammary gland by the determination unit 44. In this selection, the selection unit 46 selects the second tomographic image group according to a second selection rule different from the first selection rule. The second selection rule according to this embodiment is a rule of selecting a tomographic image group other than the tomographic image, in which the tumor candidate region determined to be the local mass of the mammary gland by the determination unit 44 is detected, among the plurality of tomographic images Dj. In the example illustrated in FIG. 7, the selection unit 46 selects the tomographic images D1, D2, D4, and D5 other than the tomographic image D3, in which the tumor candidate region K32 is detected, as the second tomographic image group.

The selection unit 46 selects a third tomographic image group from the plurality of tomographic images Dj in a third region other than the first region and the second region. In this selection, the selection unit 46 selects the third tomographic image group according to a third selection rule different from the first selection rule and the second selection rule. The third selection rule according to this embodiment is a rule of selecting all of the plurality of tomographic images Dj. In the example illustrated in FIG. 7, the selection unit 46 selects the tomographic images D1 to D5 as the third tomographic image group.

Figure 8:
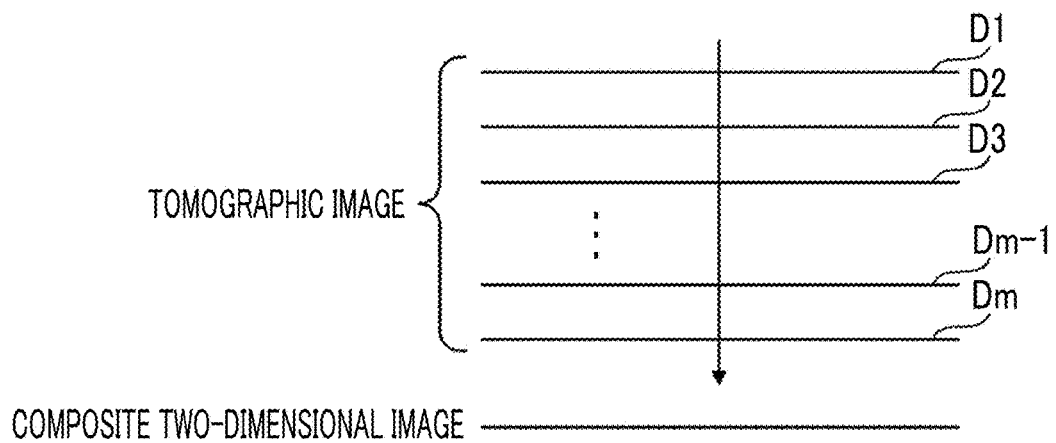
FIG. 8 is a diagram illustrating a composite two-dimensional image generation process.

The combination unit 48 generates a composite two-dimensional image using the tomographic image groups selected by the selection unit 46 for each of the first region, the second region, and the third region. The composite two-dimensional image is a pseudo two-dimensional image corresponding to a simple two-dimensional image that is captured by irradiating the breast M with the radiation emitted at the reference radiation source position Sc. In this embodiment, the combination unit 48 combines the pixel values of the corresponding pixels in each of the tomographic images Dj along a viewing direction from the reference radiation source position Sc to the radiation detector 15, that is, along the optical axis X0 illustrated in FIG. 5 in a state in which the plurality of tomographic images Dj are stacked as illustrated in FIG. 8 to generate a composite two-dimensional image. Hereinafter, a specific example of a composite two-dimensional image generation process will be described.

Figure 9:
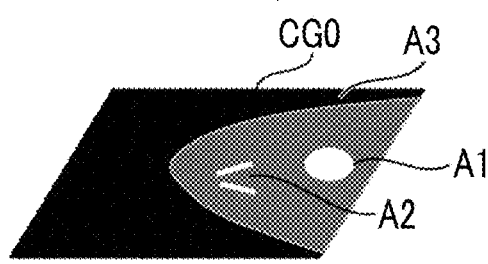
FIG. 9 is a diagram illustrating an example of a composite two-dimensional image.

FIG. 9 illustrates an example of a composite two-dimensional image CG0. As illustrated in FIG. 9, for a first region A1, the tumor candidate regions K21, K31, and K41 determined to be the tumor in the tomographic images D2 to D4 are combined. In the case of this combination, the combination unit 48 sets an added average value of the pixel values of the pixels at the corresponding pixel position in a plurality of tumor candidate regions as the pixel value of the composite two-dimensional image CG0. In addition, in the case of this combination, for the pixel at the pixel position included in only one of the plurality of tumor candidate regions, the combination unit 48 sets the pixel value of the pixel as the pixel value of the composite two-dimensional image CG0. Further, for example, the combination unit 48 may set the largest region, the smallest region, or an average region of the regions among the plurality of tumor candidate regions as the first region A1 and may set the added average value of the pixel values of each pixel of the first region A1 in the selected tomographic image group as the pixel value of the composite two-dimensional image CG0.

In addition, as illustrated in FIG. 9, for a second region A2, the regions, which correspond to the tumor candidate region K32 of the tomographic image D3 determined to be the local mass of the mammary gland, in the tomographic images D1, D2, D4, and D5 are combined. In the case of this combination, the combination unit 48 sets the added average value of the pixel values of each pixel included in the second region A2 in each of the tomographic images D1, D2, D4, and D5 as the pixel value of the composite two-dimensional image CG0.

Further, as illustrated in FIG. 9, for a third region A3, the corresponding regions of the tomographic images D1 to D5 are combined. In the case of this combination, the combination unit 48 sets the added average value of the pixel values of each pixel included in the third region A3 in each of the tomographic images D1 to D5 as the pixel value of the composite two-dimensional image CG0.

The display control unit 50 performs control to display the composite two-dimensional image CG0 generated by the combination unit 48 on the display 23.

Next, the operation of the image processing device 4 according to this embodiment will be described with reference to FIG. 10. The CPU 20 executes the image processing program 30 to perform a composite two-dimensional image generation process illustrated in FIG. 10. The composite two-dimensional image generation process illustrated in FIG. 10 is performed, for example, in a case in which the user inputs an execution start instruction through the input device 24.

Figure 10:
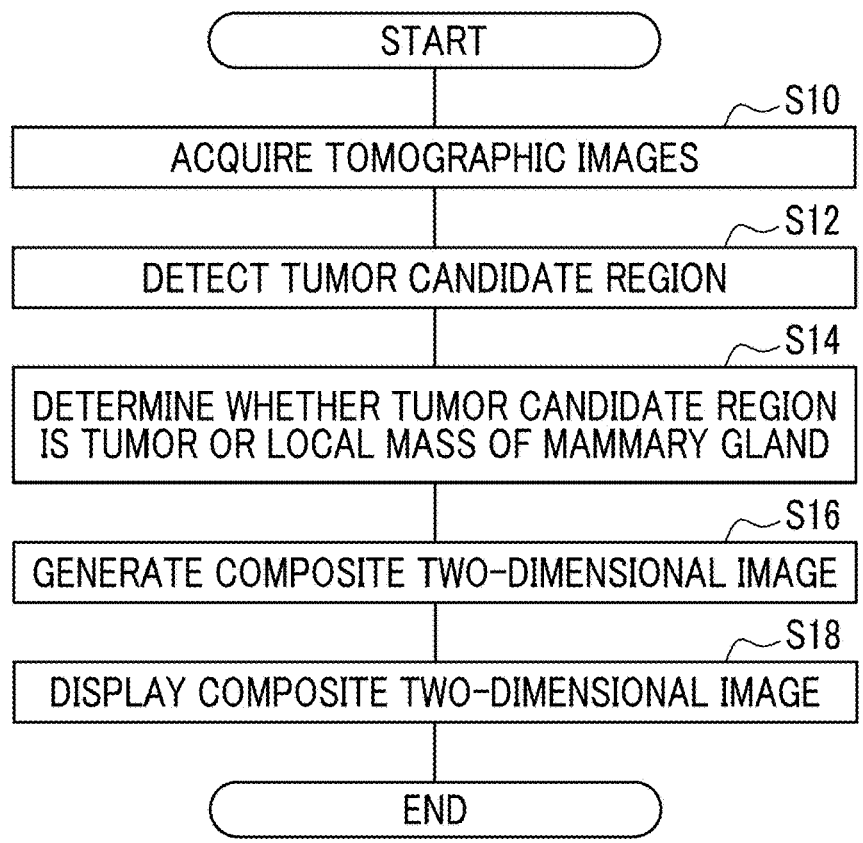
FIG. 10 is a flowchart illustrating an example of the composite two-dimensional image generation process.

In Step S10 of FIG. 10, the acquisition unit 40 acquires a plurality of tomographic images Dj generated by the tomosynthesis imaging performed by the mammography apparatus 1 under the control of the console 2. In Step S12, the detection unit 42 detects the tumor candidate region from the plurality of tomographic images Dj acquired in Step S10 as described above.

In Step S14, the determination unit 44 determines whether each of the tumor candidate regions detected in Step S12 is the tumor or the local mass of the mammary gland as described above. In Step S16, the selection unit 46 selects the first tomographic image group from the plurality of tomographic images Dj according to the first selection rule in the first region determined to be the tumor in Step S14 as described above. In addition, the selection unit 46 selects the second tomographic image group from the plurality of tomographic images Dj according to the second selection rule in the second region determined to be the local mass of the mammary gland in Step S14 as described above. Further, the selection unit 46 selects the third tomographic image group from the plurality of tomographic images Dj according to the third selection rule in the third region other than the first region and the second region as described above. Then, the combination unit 48 generates the composite two-dimensional image CG0 using the tomographic image groups selected by the selection unit 46 for each of the first region, the second region, and the third region as described above.

In Step S18, the display control unit 50 performs control to display the composite two-dimensional image CG0 generated in Step S16 on the display 23 as described above. In a case in which the process in Step S18 ends, the composite two-dimensional image generation process ends.

As described above, in the composite two-dimensional image generation process according to this example, the second tomographic image group used for generating the second region A2 of the composite two-dimensional image CG0 is a tomographic image group (the tomographic images D1, D2, D4, and D5) other than the tomographic image D3, in which the tumor candidate region K32 determined to be the local mass of the mammary gland is detected, among the plurality of tomographic images Dj. Therefore, the local mass of the mammary gland that looks like the tumor in the simple two-dimensional image is not represented in the composite two-dimensional image CG0 illustrated in FIG. 9. As a result, in the composite two-dimensional image CG0 illustrated in FIG. 9, it is suppressed that the local mass of the mammary gland is erroneously recognized as the tumor.

As described above, according to this embodiment, it is possible to generate the composite two-dimensional image having the same diagnostic performance as the tomographic image. Therefore, a diagnostician, such as a doctor, need only interpret one composite two-dimensional image. Therefore, an interpretation burden is reduced. In addition, the tomographic image that is no longer needed for interpretation is deleted from the storage device to save the capacity of the storage device.

Figure 11:
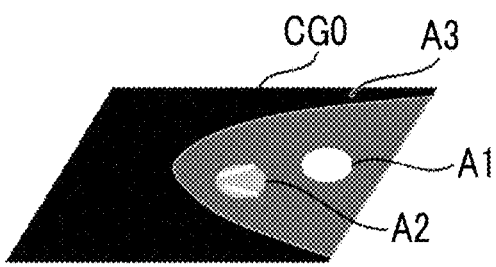
FIG. 11 is a diagram illustrating an example of the composite two-dimensional image.

In addition, in the above-described embodiment, the case in which a tomographic image group other than the tomographic image, in which the tumor candidate region determined to be the local mass of the mammary gland is detected, among the plurality of tomographic images Dj is applied as the second tomographic image group has been described. However, the present disclosure is not limited thereto. For example, the tomographic image, in which the tumor candidate region determined to be the local mass of the mammary gland is detected, and a tomographic image of a layer adjacent to the tomographic image among the plurality of tomographic images Dj may be applied as the second tomographic image group. In this case, as in the composite two-dimensional image CG0 illustrated in FIG. 11 as an example, in the second region A2, the tumor candidate region K32 of the tomographic image D3 determined to be the local mass of the mammary gland and the mammary gland N41 of the tomographic image D4 of the layer adjacent to the tomographic image D3 are combined. Therefore, in the composite two-dimensional image CG0 illustrated in FIG. 11, the tumor candidate region K32 is clearly represented as the local mass of the mammary gland by the combination of the tumor candidate region K32 and the mammary gland N41. Therefore, even in the composite two-dimensional image CG0 illustrated in FIG. 11, it is suppressed that the local mass of the mammary gland is erroneously recognized as the tumor.

Figure 12:
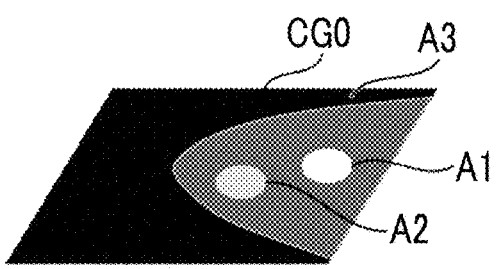
FIG. 12 is a diagram illustrating an example of the composite two-dimensional image.

Further, for example, the same tomographic image group as the third tomographic image group may be applied as the second tomographic image group. In this case, the second selection rule and the third selection rule are the same rule. Furthermore, in this case, the combination unit 48 generates the composite two-dimensional image CG0 in which the density of the second region A2 in the composite two-dimensional image CG0 is controlled to be close to the density of the third region A3. In this case, as illustrated in FIG. 12 as an example, the density of the pixel in the second region A2 is closer to the density of the pixel in the third region A3 than to the density of the pixel in the first region A1. Therefore, the second region A2 can be clearly distinguished from the region of the tumor. Therefore, even in the composite two-dimensional image CG0 illustrated in FIG. 12, it is suppressed that the local mass of the mammary gland is erroneously recognized as the tumor.

Figure 13:
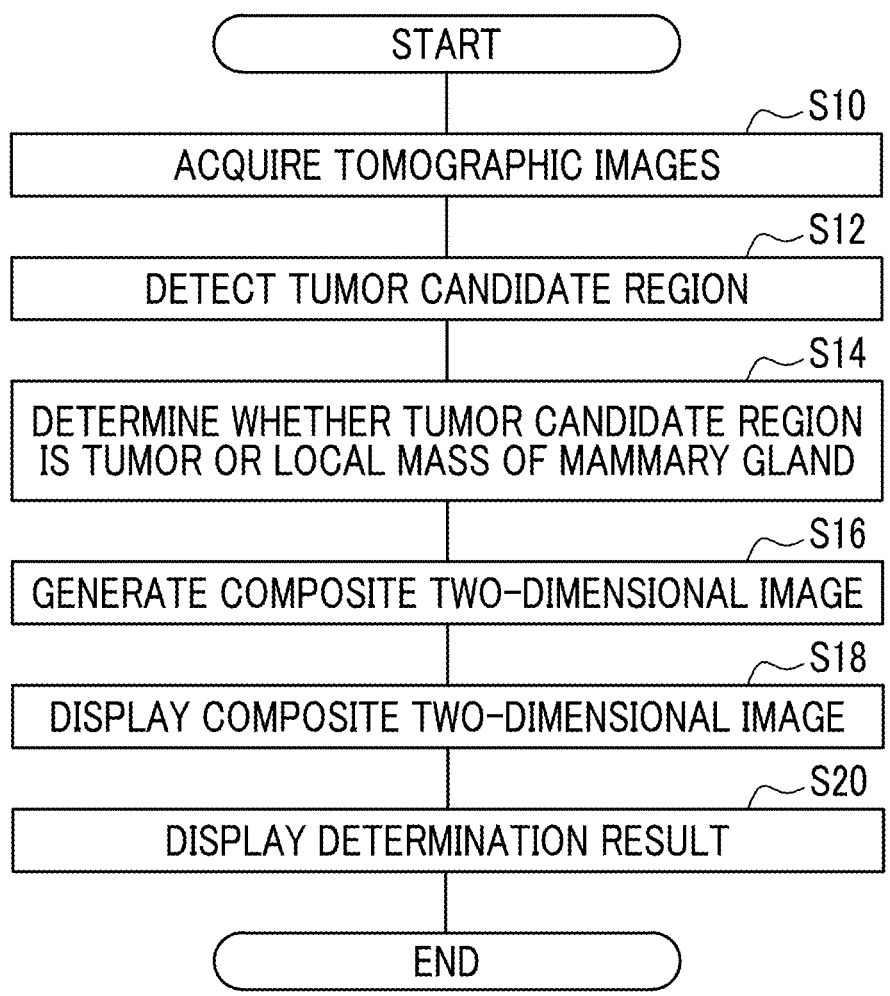
FIG. 13 is a flowchart illustrating another example of the composite two-dimensional image generation process.
Figure 14:
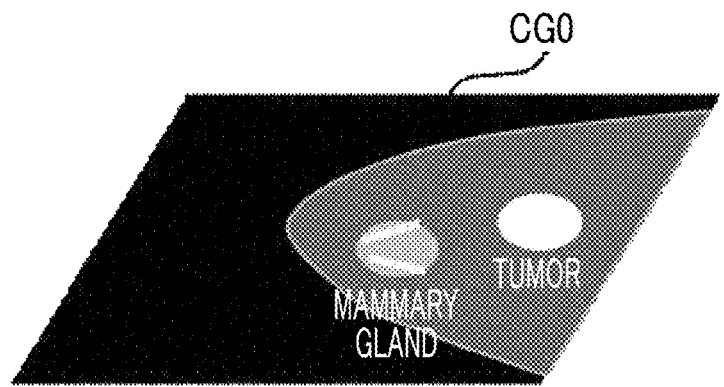
FIG. 14 is a diagram illustrating an example of a display state of a determination result.

In the flowchart illustrated in FIG. 10, only the composite two-dimensional image CG0 is displayed. However, the display control unit 50 may perform Step S20 of displaying the determination result of the determination unit 44, in addition to Step S18 of displaying the composite two-dimensional image CG0, as illustrated in a flowchart of FIG. 13. In Step S20, the display control unit 50 performs control to display the determination result of the determination unit 44 indicating whether the tumor candidate region is the tumor or the local mass of the mammary gland on the composite two-dimensional image CG0. FIG. 14 illustrates an example of the display state of the determination result. As illustrated in FIG. 14, the display control unit 50 performs control to display a character string indicating the determination result of the determination unit 44 in the vicinity of the tumor candidate region to be determined. In the example illustrated in FIG. 14, a character string "mammary gland" is displayed below the tumor candidate region determined to be the local mass of the mammary gland, and a character string "tumor" is displayed below the tumor candidate region determined to be the tumor.

Figure 15:
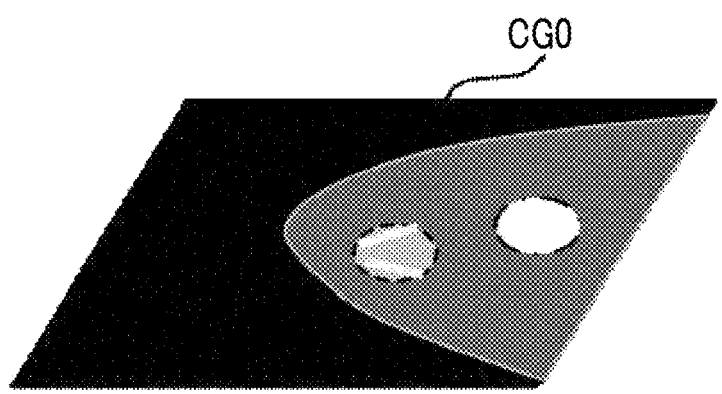
FIG. 15 is a diagram illustrating an example of the display state of the determination result.

In addition, as illustrated in FIG. 15, the display control unit 50 may perform control to display the determination result of the determination unit 44 such that the border color of the tumor candidate region to be determined is different. In the example of FIG. 15, the border of the tumor candidate region determined to be the local mass of the mammary gland is displayed as a broken line, and the border of the tumor candidate region determined to be the tumor is displayed as a one-dot chain line. However, this indicates that the border colors are different.

Figure 16:
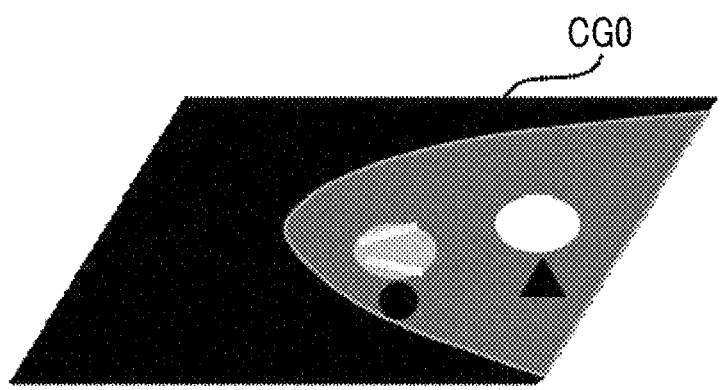
FIG. 16 is a diagram illustrating an example of the display state of the determination result.

Further, as illustrated in FIG. 16, the display control unit 50 may perform control to display a mark indicating the determination result of the determination unit 44 in the vicinity of the tumor candidate region to be determined. In an example illustrated in FIG. 16, a circular mark is displayed below the tumor candidate region determined to be the local mass of the mammary gland, and a triangular mark is displayed below the tumor candidate region determined to be the tumor.

In addition, in the above-described embodiment, the case in which all of the plurality of tomographic images Dj are applied as the third tomographic image group has been described. However, the present disclosure is not limited thereto. For example, a tomographic image group, in which the absolute value of the difference between the pixel value of a pixel of interest and the average value of the pixel values of the pixels of interest in all of the plurality of tomographic images Dj is equal to or greater than a preset threshold value, among the plurality of tomographic images Dj may be applied as the third tomographic image group. Further, for example, a group of a preset number of tomographic images in descending order of the variance value of the pixel values of a region of interest including the pixel of interest among the plurality of tomographic images Dj may be applied. Furthermore, for example, a tomographic image group including the pixels whose edges have been detected by an edge detection process among the plurality of tomographic images Dj may be applied as the third tomographic image group.

Further, in the above-described embodiment, the case in which the added average value of the pixel values of the corresponding pixels in the selected tomographic image group is applied as the pixel value of the pixel of the composite two-dimensional image CG0 has been described. However, the present disclosure is not limited thereto. A median value, a maximum value, or a minimum value of the pixel values of the corresponding pixels in the selected tomographic image group may be applied as the pixel value of the pixel of the composite two-dimensional image CG0.

In addition, in the above-described embodiment, for example, the following various processors can be used as a hardware structure of processing units performing various processes, such as the acquisition unit 40, the detection unit 42, the determination unit 44, the selection unit 46, the combination unit 48, and the display control unit 50. The various processors include, for example, a CPU which is a general-purpose processor executing software (programs) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the image processing program 30 is stored (installed) in the storage unit 22 in advance has been described. However, the present disclosure is not limited thereto. The image processing program 30 may be recorded on a recording medium, such as a compact disc read only memory (CD-ROM), a digital versatile disc read only memory (DVD-ROM), or a universal serial bus (USB) memory, and then provided. In addition, the image processing program 30 may be downloaded from an external device through a network.

What is claimed is:

1. An image processing device comprising:
   at least one processor,
   wherein the processor detects a tumor candidate region from a plurality of tomographic images indicating a plurality of tomographic planes of an object,
   determines whether each of the detected tumor candidate regions is a tumor or a local mass of a mammary gland,
   selects three tomographic image groups comprising a first tomographic image group, a second tomographic image group, and a third tomographic image group, wherein:
      the at least one processor selects the first tomographic image group from the plurality of tomographic images according to a first selection rule in which a first region determined to be the tumor is detected,
      the at least one processor selects the second tomographic image group from the plurality of tomographic images according to a second selection rule in which a second region determined to be the local mass of the mammary gland is detected, and
      the at least one processor selects the third tomographic image group from the plurality of tomographic images according to a third selection rule in which a third region other than the first region and the second region is detected, and
   generates a composite two-dimensional image using the tomographic image groups selected for each of the first region, the second region, and the third region.

2. The image processing device according to claim 1, wherein the first tomographic image group is a tomographic image group in which the tumor candidate region determined to be the tumor is detected among the plurality of tomographic images.

3. The image processing device according to claim 1, wherein the second tomographic image group is a tomographic image group other than a tomographic image in which the tumor candidate region determined to be the local mass of the mammary gland is detected among the plurality of tomographic images.

4. The image processing device according to claim 2, wherein the second tomographic image group is a tomographic image group other than a tomographic image in which the tumor candidate region determined to be the local mass of the mammary gland is detected among the plurality of tomographic images.

5. The image processing device according to claim 1, wherein the second tomographic image group includes a tomographic image in which the tumor candidate region determined to be the local mass of the mammary gland is detected and a tomographic image of a layer adjacent to the tomographic image among the plurality of tomographic images.

6. The image processing device according to claim 2, wherein the second tomographic image group includes a tomographic image in which the tumor candidate region determined to be the local mass of the mammary gland is detected and a tomographic image of a layer adjacent to the tomographic image among the plurality of tomographic images.

7. The image processing device according to claim 1, wherein the second tomographic image group is the same tomographic image group as the third tomographic image group, and
   the processor generates the composite two-dimensional image in which a density of the second region has been controlled to be close to a density of the third region.

8. The image processing device according to claim 2, wherein the second tomographic image group is the same tomographic image group as the third tomographic image group, and
   the processor generates the composite two-dimensional image in which a density of the second region has been controlled to be close to a density of the third region.

9. The image processing device according to claim 1, wherein the third tomographic image group is all of the plurality of tomographic images, a tomographic image group, in which an absolute value of a difference between a pixel value of a pixel of interest and an average value of the pixel values of the pixels of interest in all of the plurality of tomographic images is equal to or greater than a preset threshold value, among the plurality of tomographic images, a group of a preset number of tomographic images in a descending order of a variance value of a pixel value of a region of interest including the pixel of interest among the plurality of tomographic images, or a tomographic image group including a pixel whose edge is detected by an edge detection process among the plurality of tomographic images.

10. The image processing device according to claim 2, wherein the third tomographic image group is all of the plurality of tomographic images, a tomographic image group, in which an absolute value of a difference between a pixel value of a pixel of interest and an average value of the pixel values of the pixels of interest in all of the plurality of tomographic images is equal to or greater than a preset threshold value, among the plurality of tomographic images, a group of a preset number of tomographic images in a descending order of a variance value of a pixel value of a region of interest including the pixel of interest among the plurality of tomographic images, or a tomographic image group including a pixel whose edge is detected by an edge detection process among the plurality of tomographic images.

11. The image processing device according to claim 1, wherein the processor performs control to display the generated composite two-dimensional image, and performs control to display a determination result of whether the tumor candidate region is the tumor or the local mass of the mammary gland on the composite two-dimensional image.

12. The image processing device according to claim 2, wherein the processor performs control to display the generated composite two-dimensional image, and performs control to display a determination result of whether the tumor candidate region is the tumor or the local mass of the mammary gland on the composite two-dimensional image.

13. An image processing method executed by a processor included in an image processing device, the image processing method comprising:
   detecting a tumor candidate region from a plurality of tomographic images indicating a plurality of tomographic planes of an object;
   determining whether each of the detected tumor candidate regions is a tumor or a local mass of a mammary gland;
   selecting three tomographic image groups comprising a first tomographic image group, a second tomographic image group, and a third tomographic image group, including:

selecting the first tomographic image group from the plurality of tomographic images according to a first selection rule in which a first region determined to be the tumor is detected;

selecting the second tomographic image group from the plurality of tomographic images according to a second selection rule in which a second region determined to be the local mass of the mammary gland is detected; and selecting the third tomographic image group from the plurality of tomographic images according to a third selection rule in which a third region other than the first region and the second region is detected; and generating a composite two-dimensional image using the tomographic image groups selected for each of the first region, the second region, and the third region.

14. A non-transitory computer-readable storage medium storing an image processing program that causes a processor included in an image processing device to execute a process comprising:

detecting a tumor candidate region from a plurality of tomographic images indicating a plurality of tomographic planes of an object;

determining whether each of the detected tumor candidate regions is a tumor or a local mass of a mammary gland;

selecting three tomographic image groups comprising a first tomographic image group, a second tomographic image group, and a third tomographic image group, including:

selecting the first tomographic image group from the plurality of tomographic images according to a first selection rule in which a first region determined to be the tumor is detected;

selecting the second tomographic image group from the plurality of tomographic images according to a second selection rule in which a second region determined to be the local mass of the mammary gland is detected; and selecting the third tomographic image group from the plurality of tomographic images according to a third selection rule in which a third region other than the first region and the second region is detected; and generating a composite two-dimensional image using the tomographic image groups selected for each of the first region, the second region, and the third region.

* * * * *